United States Patent
Novak et al.

(10) Patent No.: US 12,296,111 B2
(45) Date of Patent: May 13, 2025

(54) TAMPER-EVIDENT HOUSING

(71) Applicant: ConvaTec Limited, Flintshire (GB)

(72) Inventors: Marian Novak, Michalovce (SK); Vladimir Curila, Michalovce (SK); David Donnelly, Flintshire (GB)

(73) Assignee: CONVATEC LIMITED, Flintshire (GB)

( * ) Notice: Subject to any disclaimer, the term of this patent is extended or adjusted under 35 U.S.C. 154(b) by 0 days.

(21) Appl. No.: 18/400,351

(22) Filed: Dec. 29, 2023

(65) Prior Publication Data

US 2024/0132256 A1 Apr. 25, 2024

Related U.S. Application Data

(63) Continuation of application No. PCT/GB2023/050049, filed on Jan. 11, 2023.

(30) Foreign Application Priority Data

Jan. 12, 2022 (GB) ...................... 2200304

(51) Int. Cl.
*A61M 25/00* (2006.01)
*B65D 41/34* (2006.01)

(52) U.S. Cl.
CPC ....... *A61M 25/002* (2013.01); *B65D 41/3447* (2013.01); *B65D 2251/0015* (2013.01); *B65D 2401/30* (2020.05)

(58) Field of Classification Search
CPC ........ B65D 41/3447; B65D 2251/0015; B65D 2401/30; A61M 25/002
See application file for complete search history.

(56) References Cited

U.S. PATENT DOCUMENTS 4,629,082 A * 12/1986 Badia Iniesta ......... B65D 41/58
215/253
4,756,438 A * 7/1988 Ryder ................ B65D 41/3447
215/252

(Continued)

FOREIGN PATENT DOCUMENTS

EP 4297835 B1 2/2024
EP 4326374 A1 2/2024

(Continued)

OTHER PUBLICATIONS

English translation of JP H08133314 (Year: 2024).*
International Preliminary Report on Patentability and corresponding Request; Dated Nov. 21, 2023; 15 pages.

*Primary Examiner* — James N Smalley
(74) *Attorney, Agent, or Firm* — TAFT STETTINIUS HOLLISTER LLP; Ryan O. White; Derek B. Lavender

(57) ABSTRACT

Disclosed is a housing for a catheter, the housing comprising: a body; a cap assembly comprising a cap and a tamper-evidence ring, wherein the cap is attached to the body and the tamper-evidence ring in an unopened configuration and is configured to be irreversibly detached from the tamper-evidence ring when the cap is removed from the body, the housing further comprising at least one anti-rotation mechanism to prevent rotation of the tamper-evidence ring upon rotation of the cap, and at least one axial retention mechanism configured to axially retain the tamper-evidence ring when irreversibly detached from the cap.

18 Claims, 6 Drawing Sheets

(56) References Cited

U.S. PATENT DOCUMENTS

| | | | | |
|---|---|---|---|---|
| 4,813,562 | A | * | 3/1989 | Begley ............... B65D 41/3428 |
| | | | | 215/252 |
| 5,137,163 | A | * | 8/1992 | Moore ............... B65D 41/3447 |
| | | | | 215/252 |
| 5,217,114 | A | * | 6/1993 | Gadberry ............ A61M 25/002 |
| | | | | 206/439 |
| 5,314,085 | A | * | 5/1994 | Collado Bonet .. B65D 41/3409 |
| | | | | 215/258 |
| 5,819,965 | A | | 10/1998 | King et al. |
| 10,287,065 | B2 | * | 5/2019 | Widmer ............. B65D 41/3409 |
| 11,957,614 | B2 | | 4/2024 | Kendrick et al. |
| 2010/0087801 | A1 | * | 4/2010 | Torstensen .......... A61M 25/002 |
| | | | | 206/364 |
| 2023/0073264 | A1 | * | 3/2023 | Kandrac ........... A61M 25/0045 |
| 2024/0050691 | A1 | | 2/2024 | Bryant |
| 2024/0050692 | A1 | | 2/2024 | Novak et al. |
| 2024/0050693 | A1 | | 2/2024 | Kandrac et al. |
| 2024/0050694 | A1 | | 2/2024 | Kandrac et al. |

FOREIGN PATENT DOCUMENTS

| | | | | |
|---|---|---|---|---|
| EP | 4326375 | A1 | 2/2024 | |
| EP | 4326376 | A1 | 2/2024 | |
| EP | 4326377 | A1 | 2/2024 | |
| EP | 4326378 | A1 | 2/2024 | |
| EP | 4326380 | A1 | 2/2024 | |
| GB | 2311060 | A | 9/1997 | |
| GB | 2435038 | A | 8/2007 | |
| JP | 08133314 | A * | 5/1996 | ......... B65D 41/3409 |
| WO | 9735773 | A2 | 10/1997 | |
| WO | 2018156589 | A2 | 8/2018 | |

* cited by examiner

TAMPER-EVIDENT HOUSING

TECHNICAL FIELD OF THE INVENTION

The present invention relates to a tamper-evident housing for storing an item or product. The tamper-evident housing is configured to be irreversibly altered when opened so as to provide an indication of the integrity of the housing to a user prior to use. In particular, though not exclusively, the housing is for use with a catheter or other medical device, especially an intermittent urinary catheter, and most especially a female intermittent urinary catheter.

BACKGROUND TO THE INVENTION

A catheter is a medical device comprising a hollow catheter tube designed for insertion into canals, vessels, passageways or body cavities to permit injection, drainage or withdrawal of fluids or substances therefrom, or to ensure said canals, vessels, passageways etc remain open. Urinary catheters are designed for use for insertion into a user's bladder via the urethra to drain the bladder.

Prior to use, the catheter is provided within a housing for transportation and storage purposes. Typically, the housing will provide a sterile compartment in which the catheter is located. To gain entry to the catheter prior to use, the housing may be opened, for example, by removing a cap. It is generally preferable, especially for intermittent urinary catheters, and most especially female intermittent urinary catheters (which are typically shorter and can thus be packaged in solid housings intended to have an appearance more akin to an item of make-up than a medical device) to provide a cap which comprises a tamper-evident attachment such that a user can guarantee that the sterility of the catheter is maintained prior to use.

The present invention seeks to provide an improved tamper-evidence mechanism for a housing.

SUMMARY OF THE INVENTION

The present invention provides a housing for a catheter according to the appended claims.

The present disclosure provides a housing for a catheter, the housing comprising: a body and a cap assembly. The cap assembly may comprise a cap and a tamper-evidence ring. The cap may be attached to the body and the tamper-evidence ring in an unopened configuration. The cap may be irreversibly detached from the tamper-evidence ring when the cap is removed from the body. That is, the cap and tamper-evidence ring may be configured to irreversibly detach from one another when the cap is removed from the body.

The housing may include at least one anti-rotation mechanism to prevent rotation of the tamper-evidence ring upon rotation of the cap.

The housing may further comprise at least one axial retention mechanism configured to axially retain the tamper-evidence ring when irreversibly detached from the cap.

The provision of an anti-rotation mechanism and an axial retention mechanism can help limit the movement of the tamper-evidence ring when the cap is being removed, thereby making the separation more abrupt and noticeable to a user. Further, the tamper-evidence ring may be retained on the body following a removal of the cap, thereby making use of the housing more convenient. Hence, for example, where the housing is used to provide a sterile containment of a catheter, the retention of the tamper-evidence ring allows the catheter to be withdrawn and used without being obstructed or a user being distracted by the movement of the ring.

Additionally, the use of both an axial retention and anti-rotational mechanisms minimizes any movement of the tamper-evidence ring. This may give the user an impression that the tamper-evidence ring forms part of the body of the housing which may be aesthetically or tactilely pleasing. On the other hand, the use of the cap assembly comprising the cap and tamper-evidence ring may allow for simple assembly of the housing with a single movement.

The axial retention mechanism may comprise corresponding inter-engaging and/or abutting portions of the body and tamper-evidence ring. Thus, either or both of the body and tamper-evidence ring may comprise at least one projection which extends towards the respective opposing one of the body or tamper-evidence ring. The at least one projection may cause an obstruction which prevents the tamper-evidence ring being removed from the body along a principal axis of the housing. Hence, once the cap has been removed and no longer prevents removal of the tamper-evidence ring, the tamper-evidence ring is retained in situ. The axial retention mechanism may be referred to as or comprise an axial retention member.

In some embodiments, the at least one axial retention mechanism may comprise at least one radial projection which extends from the body to engage with the tamper-evidence ring. The at least one radial projection may comprise a pedestal, flange, rib or tooth, for example. The at least one radial projection may extend circumferentially so as to have an arcuate length around the principal axis of the housing. The at least one projection may extend radially beyond the radial location of an internal surface of the tamper-evidence ring. The at least one axial retention mechanism may comprise at least one axially facing surface which faces towards the axial retention ring and body. The the at least one axial retention mechanism may comprise a radial projection which extends into a recess or gap provided between the cap and tamper-evidence ring. The axial retention mechanism may be provided in the annular gap between the cap and tamper-evidence ring.

There may be a plurality of axial retention mechanisms circumferentially distributed around the body and/or tamper-evidence ring. In some embodiments, there may be between two and six axial retention mechanisms, optionally four axial retention mechanisms.

The tamper-evidence ring may form a unitary body with the cap. The tamper-evidence ring and cap may be co-formed as a single object, for example, by injection moulding. The tamper-evidence ring and cap may be adjoined or attached to one another via a plurality of severable connectors which extend therebetween. The severable connectors may be configured to break upon rotation and/or axial separation of the cap from the body.

The cap and tamper-evidence ring may be separated via an annular gap which is bridged by the plurality of severable connectors.

There may be a plurality of severable connectors. There may be between two and six severable connectors, optionally four severable connectors. The plurality of severable connectors may be circumferentially distributed, optionally evenly distributed, around cap assembly. The separation between the cap and the tamper-evidence ring may be between 0.5 mm and 3 mm. In some embodiments the separation may be 1 mm.

The connectors may be configured to sever proximate to the cap. The connectors may be tapered so as to reduce in thickness from the tamper-evidence ring to the rim of the cap, thereby providing a weakened region local to the rim of the cap.

The axial retention mechanisms may be positioned circumferentially between the severable connectors.

The at least one axial retention mechanism may comprise a rigid member over which the cap assembly is deformably fitted during assembly of the housing. The cap assembly, particularly the tamper-evidence ring, may be suitably flexible so as to deform from a resting shape when forced over the axial retention mechanism prior to returning to the resting shape when past the axial retention mechanism. To aid fitting of the cap assembly, the axial retention mechanisms may comprise an ramp which slidably receives a free end of the tamper-evidence ring when the cap assembly is mounted to the body. The at least one projection may comprise a tamper-evidence ring facing surface and a cap facing surface. The cap facing surface may comprise the ramp for receiving the free end edge of the tamper-evidence ring.

The anti-rotation mechanism may comprise corresponding inter-engaging and/or abutting portions of the body and tamper-evidence ring. Thus, either or both of the body and tamper-evidence ring may comprise at least one anti-rotation projection which extends towards the respective opposing one of the body or tamper-evidence ring. The at least one projection may cause an obstruction which prevents the tamper-evidence ring being rotated about the principal axis of the housing. Hence, during and after removal of the cap, the tamper-evidence ring is retained in the same angular position. The anti-rotation mechanisms may be referred to as or comprise an anti-rotation member.

It will be appreciated that some rotational movement may be permitted, for example, a few degrees of movement in either direction between a first rotational position and a second rotational position, but the anti-rotation mechanism generally prevents free rotation. The anti-rotation mechanism may prevent the cap being removed from the body until the severable connectors have been severed.

The anti-rotation mechanism may comprise at least one radial projection which extends from the body and engages with the tamper-evidence ring. The anti-rotation projection may be received within a recess or opening in the opposite one of the body or tamper-evident ring. The projection may be snugly received within the recess or opening. The projection may engage with a terminal edge of the tamper-evidence ring. The terminal edge may be the terminal edge of the cap assembly. The opening or recess may be provided in the terminal edge.

The projection may comprise a one or more circumferentially facing surface which abuts an opposing circumferentially facing surface of the tamper-evidence ring. The circumferentially facing surface may extend parallel to the longitudinal axis of the housing or may be inclined relative to the longitudinal axis and inclined circumferentially. In some embodiments, the projection may be triangular when viewed radially inwards. The projection may comprise a sloped surface. The sloped surface may face towards the right when viewed radially inwards, such that the sloping face receives a corresponding opposing surface of the tamper-evidence ring when being screwed in a clockwise direction onto the body. In the alternative, the sloped surface may face towards the left when viewed radially inwards, such that the sloping face receives a corresponding opposing surface of the tamper-evidence ring when being screwed in an anti-clockwise direction onto the body.

The anti-rotation projection may be configured to allow the tamper-evidence ring to rotate in first rotational direction and obstruct rotation in a second rotational direction. The anti-rotation mechanism may comprise a circumferentially facing ramp to allow rotation in a/the first direction. The circumferentially facing ramp may be the sloped surface of the projection. The projection may comprise the circumferentially facing ramps on a first surface. The projection may comprise a second surface on a circumferentially opposing side of the projection to the first surface. The second surface may be perpendicular to the second rotational direction. The second surface may extend parallel to the longitudinal axis of the housing. The cap assembly may be attached in a clockwise direction. Hence, the first rotational direction may be clockwise and the second rotational direction may be anti-clockwise when viewed end on from the cap end.

The anti-rotation mechanism and the axial retention mechanism may be axially separated from one another. The axial retention mechanism may be provided towards the cap end of the tamper-evidence ring. The anti-rotation mechanism may be provided at the free end of the tamper-evidence ring. The axial retention mechanism may engage with an end face of the cap end of the tamper-evidence ring. The anti-rotation mechanism may engage with a rim of the free end of the tamper-evidence ring.

Either or both of the axial retention mechanism and the anti-rotational mechanism may be viewable from the exterior of the housing when the cap assembly is attached to the body. By providing the axial retention mechanism and the anti-rotational mechanism of the cap assembly in a visible position it is possible to readily determine when the cap assembly has been properly attached to the body and also to determine whether the cap assembly remains properly attached to the body prior to removing the cap.

The body and/or tamper-evidence ring may comprise at least one spacer member to maintain the spacing of the tamper-evidence ring relative to the body. The spacer member may comprise one or more projections which project from the body, such as a rim, flange ridge, wall, pedestal or castellation. In some embodiments, the spacer member may be radially inwards of the tamper-evidence ring and configured to limit the radial deflection of the tamper-evidence ring. The spacer member may comprise an annular projection which extends radially from the body. The annular projection may comprise a full annular member or a broken annular member comprising one or more discrete arcuate sections. The annular member may be interposed by one or more anti-rotation projections. Hence, the annular projection may be a partial annulus having opposing terminal ends, wherein the anti-rotation projection may be provided between the opposing terminal ends.

The housing may comprise a plurality of axially separated spacers. A first spacer may be provided towards the free end of the tamper-evidence ring. A second spacer may be provided towards a cap end of the tamper evidence ring. The first and second spacers may both comprise annular projections which are parallel to one another. The spacer may be coaxially and concentrically arranged in relation to the body.

The cap may attach to the body in any suitable manner. The cap may be attached linearly so as to be removable in an axial direction without rotation. For example the cap may be attached via a friction or interference fit with the body. In some embodiments, the cap may be rotatably attached to the body. The cap may be attached to the body via a threaded engagement. Rotation of the cap in the first rotational direction may tighten the threaded engagement. Rotation of the cap in the second rotational direction may release the threaded engagement.

The body may comprise an outermost external surface which is axially adjacent to the tamper-evidence ring. The body may be separated from the tamper-evidence ring by a gap. The gap may be annular. The outermost external surface of the body and an external surface of the tamper-evidence ring may be flush on either side of the gap. The external surface of the tamper-evidence ring may be flush with an external surface of the cap. In some embodiments, the tamper-evidence ring may be radially inset with respect to the outer surface of the body. The outermost external surface of the body is flush with an external surface of the tamper-evidence ring and/or an external surface of the cap. An external surface of the tamper-evidence ring may be radially inwards or radially outwards of the outermost external surface of the body and/or an external surface of the cap.

The outermost external surface of the body and/or tamper-evidence ring and/or cap may be non-round. That is, the radial distance between the outermost external surface of the body and/or tamper-evidence ring and/or the cap, and the central axis of the body, may vary circumferentially about the central axis such that the cross-section which is transverse to the longitudinal axis may be non-circular.

In some embodiments, the radial thickness of the tamper-evidence ring may vary circumferentially. As such, the tamper-evidence ring may be thicker in some circumferential locations than others. The tamper-evidence ring and/or cap may be non-circular so as to have one or more corner regions or lobes. The corner regions or lobes may provide a preferential profile for grasping and rotating the cap to remove the cap. In the case of the tamper-evidence ring, where the external surface comprises at least one corner region the severable connectors may be provided at the at least one corner region.

In the case of the tamper-evidence ring, the or each corner region may comprise a recess. The or each recess may be on an external surface of the tamper-evidence ring. The or each recess may extend circumferentially. The or each recess may extend circumferentially through the entire corner region or lobe. The depth of the recess(es) may vary circumferentially. The depth of the recess(es) may vary such that the radial thickness of the tamper-evidence ring is constant at one axial location.

The provision of recesses in each of the lobes or corner regions of the tamper-evidence ring reduces the amount of material used in these regions whilst maintaining the improved grip the corners provide the user.

The internal surface of the tamper-evidence ring and/or cap and/or body may be round, e.g. circular, whereas the external surface may be out of round, i.e. non-circular, for example a "squircle". In the case of the tamper-evidence ring, where the external surface comprises a recess, the external surface may be round at the axial location of the recess.

The radial thickness of the tamper-evidence ring may vary axially. As such, an internal surface of the tamper evidence ring may taper. The taper may be provided on the free end so as to provide a wider opening for receiving the body portion and, optionally, receiving the axial retention mechanism and/or the anti-rotational mechanism. The taper may reduce the radial thickness of the tamper-evidence ring by 50%. The axial extent of the taper may be less than 50% of the axial length of the tamper-evidence ring, optionally less than 25%, optionally less than 10%.

The tamper-evidence ring may comprise a resiliently deformable material such that it can be expanded and/or deformed whilst being attached to the body. As such, the tamper-evidence ring may be configured to expand and/or deform when passing over the axial retention mechanism and/or the anti-rotation mechanism when being fitted to the body.

The housing may comprise a catheter. The catheter may be a urinary catheter. The catheter may be an intermittent catheter. The catheter may be a female catheter (i.e. a catheter intended for use by a female and adapted to the female anatomy). The catheter may be a female intermittent urinary catheter.

The invention also provides a method of assembling a housing according to the aspect of the invention set out above (optionally including any optional features); the method comprising applying the cap assembly to the body, such that when the cap is removed, the tamper evidence ring remains attached to the body. The method of assembly may comprise screwing the cap onto the body. The method of assembly may comprise screwing the cap onto the body such that the tamper evidence ring deforms when passing over the axial retention mechanism and/or the anti-rotation mechanism when being fitted to the body.

The invention also provides a method of opening a housing according to the aspect of the invention set out above (optionally including any optional features); the method comprising removing the cap of cap assembly from the body, such that the tamper evidence ring remains attached to the body. The method may comprise removing the catheter from the body. The method may comprise returning the catheter to the body, then returning the cap to the body. The method may comprise using the catheter, e.g. to drain the bladder, prior to returning it to the body. The method of removing the cap may be unscrewing the cap (for example unscrewing it anticlockwise), and the method of returning the cap to the body may comprise screwing the cap (e.g. screwing it clockwise).

The skilled person will appreciate that except where mutually exclusive, a feature described in relation to any one of the aspects, embodiments or examples described herein may be applied mutatis mutandis to any other aspect, embodiment or example. Furthermore, except where mutually exclusive, any feature described herein may be applied to any aspect and/or combined with any other feature described herein.

BRIEF DESCRIPTION OF THE DRAWINGS

In order that the invention may be more clearly understood one or more embodiments thereof will now be described, by way of example only, with reference to the accompanying drawings, of which.

DETAILED DESCRIPTION OF THE INVENTION

In the following detailed description, numerous specific details are set forth in order to provide a thorough understanding of various embodiments and the inventive concept. However, those skilled in the art will understand that the present invention may be practiced without these specific details or with known equivalents of these specific details, that the present invention is not limited to the described embodiments, and that the present invention may be practiced in a variety of alternative embodiments. It will also be appreciated that well known methods, procedures, components, and systems may have not been described in detail.

The following description focusses on a housing for use with a catheter, specifically an intermittent female urinary catheter. However, it will be appreciated that the housing may be employed elsewhere and the example of a catheter housing is not intended to restrict the scope of the present disclosure.

Figure 1:
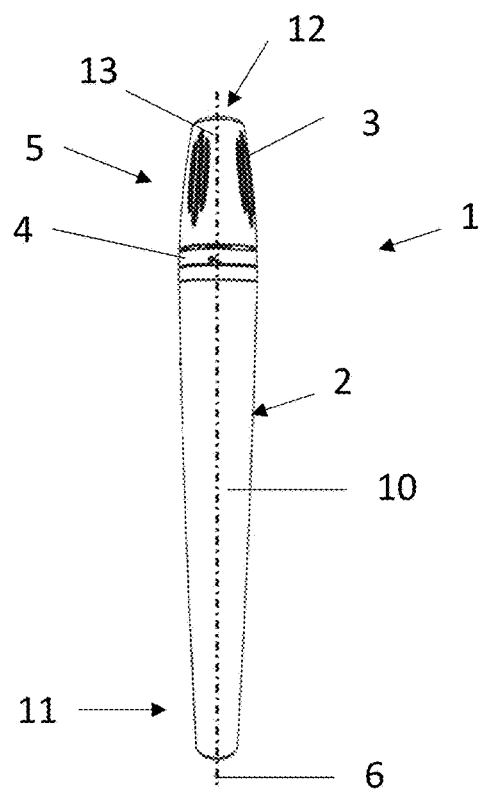
FIG. 1 shows a side view of a housing according to the present invention.
Figure 7:
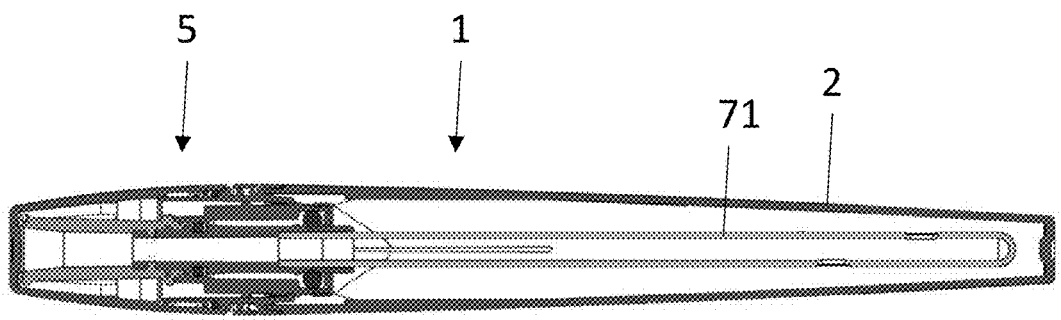
FIG. 7 shows a longitudinal section view of the housing comprising a female intermittent urinary catheter.

FIG. 1 shows an external housing 1 for a catheter 71 (shown only in FIG. 7). The housing 1 may comprise a main body 2 in which the catheter 71 is predominantly housed, a cap 3 which is detachable from the body 2 by a user prior to use, and a tamper-evidence ring 4 which is configured to be irreversibly altered when the cap 3 is moved relative to the body. The movement of the cap 3 which irreversibly alters the tamper-evidence ring 4 may correspond to the housing being opened, the cap being partially or fully removed, or a seal which preserves the integrity of the enclosed volume of the housing 1 being broken. The cap 3 and tamper-evidence ring 4, may be collectively referred to as a cap assembly 5. Removing the cap 3 exposes the catheter 71 such that it can be withdrawn from the body 1. An example of a catheter 71 which may be utilised with the housing 1 is shown in FIG. 7 and described further below.

The housing 1 provides an enclosed volume in which the catheter 71 can be housed for storage and transportation prior to use. Further, the housing 1 may be sealed so as to provide a sterile cavity in which the catheter 71 is located. The housing 1 may also be used to house the catheter 71 following use and for disposal.

The housing 1 is generally tubular and elongate having a longitudinal axis 6 which may be referred to as the principal or central axis of the housing 1. References to a longitudinal axis 6, axis, axial, radial or circumferential in this disclosure should be taken to be with reference to the longitudinal axis 6 unless stated otherwise. It should be noted that although the housing described herein is tubular and elongate this is not a limitation and other shapes of housing may employ the tamper-evidence mechanism described herein.

Figure 2:
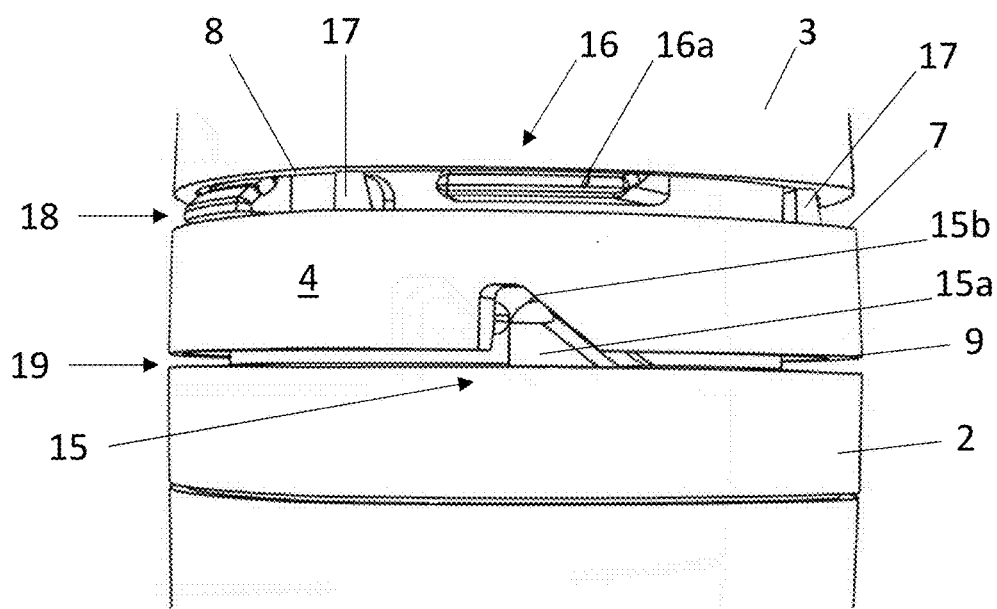
FIG. 2 shows an enlarged view of the tamper-evidence ring, body and terminal end of the cap of the housing of FIG. 1.

With reference to FIGS. 1 and 2, the tamper-evidence ring 4 may comprise a cap-end 7 which is proximate and/or adjacent to the open end 8 of the cap 3, and a free-end 9 (which may be referred to as a body-end) which may receive and be proximate and/or adjacent to the body 2.

The enclosed volume provided by the housing 1 is defined by an external wall 10 of the housing 1 which extends from a first closed end 11 to a second closed end 12 provided by the cap 3. The wall 10 provides a fully enclosed space in the described embodiment and does not include any unsealed apertures or openings prior to opening thereby allowing the interior of the housing 1 to be sterile. The wall 10 will generally comprise portions of the body 2 and cap 3 with the tamper-evidence ring 4 being located externally of the wall 10 and not providing part of the housing structure which encloses or defines the internal volume.

The external profile of the housing 1 can be any required for aesthetic or functional purposes and, in the example shown, is generally cylindrical, tapering towards the first end 11 and second end 12 to aid insertion into a storage receptacle or pocket, for example.

The cap 3 comprises an open-ended generally tapered cylindrical enclosure having a circumferential external wall which extends coaxially along the longitudinal axis 6, and a radially extending, axially facing end wall 13 which provides the closed end at the terminal end of the cap 3 and external housing 1. The cap 3 mates with and covers the open end of the main body 2, such that the main body 2 is received within the open end 8 of the cap 3. However, it will be appreciated that the cap 3 could be received within an open end of the main body 2 in some embodiments.

Figure 4:
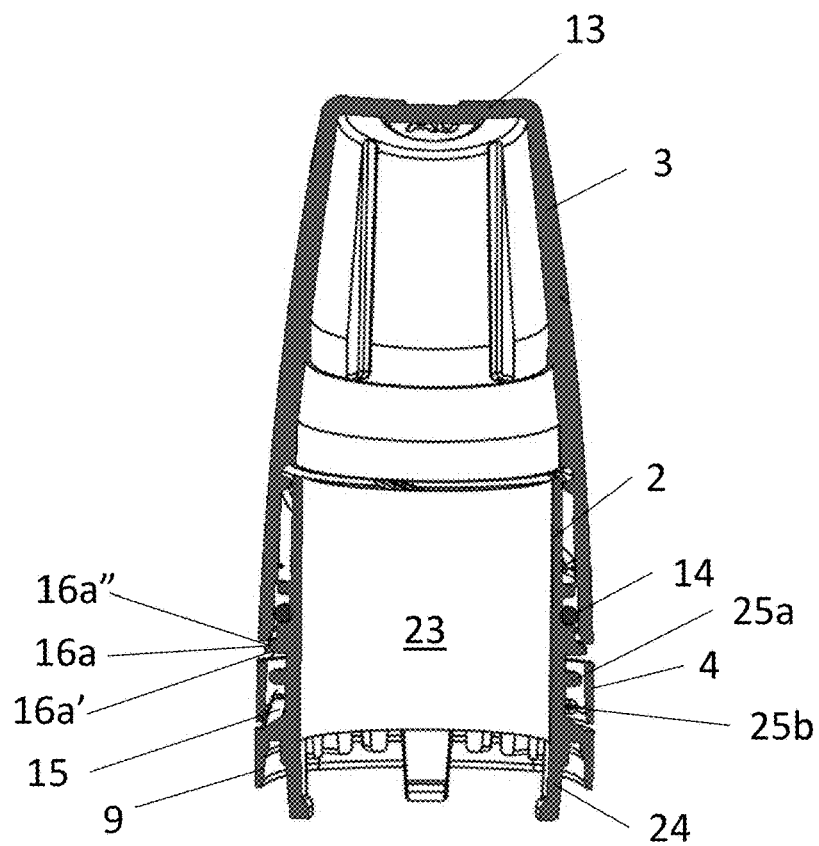
FIG. 4 shows a longitudinal section of the cap assembly attached to the body.

As shown in FIG. 4, a seal 14 may be provided between the cap 3 and main body 2 to preserve the sterility of the internal volume of the external housing 1, prior to use. In the example shown, the seal 14 is in the form of an O-ring located in a channel provided between radially opposing walls of the cap 3 and body 2. Hence, whilst the cap 3 is located on the body 2 and attached to the tamper-evidence ring 4, the hermetic seal 14 maintains the sterility of the internal volume. Further, in order to remove the cap 3 to an extent that the hermetic seal between the cap 3 and body 2 is broken/opened, the tamper-evidence ring 4 must also be broken, thereby providing an indication and reassurance to a user that the hermetic seal is intact if the cap assembly 5 is intact prior to use.

Generally, it will be appreciated that the use of the term 'removal' in relation to the cap 3 may relate to a full removal of the cap 3 from the body 2 such that the cap 3 and body 2 cease to be directly connected or in contact with one another, or may relate to the cap 3 being removed to an extent that the hermetic seal 14 is permanently or temporarily broken and the sterility of the internal volume can no longer be guaranteed. It will also be appreciated that other types of seal, hermetic or otherwise, may be employed with the housing 1 of the present disclosure. Further, the housing 1 may not be sealed in some embodiments.

The cap 3 and/or main body 2 may generally be substantially rigid so as to provide protection for the catheter 71 during transportation and to preserve integrity of the enclosed volume and maintain sterility. However, it will be appreciated that the cap 3 and/or main body 2 may be configured to provide a small amount of deformation to assist with the interference fit between the cap 3 and main body 2, for example.

The attachment of the cap 3 to the body 2 may be provided by the tamper-evidence ring 4 and/or by a direct attachment to the body 2. The tamper-evidence ring 4 may be configured such that removal of the cap 3 from the body 2 results in an irreversible detachment of the tamper-evidence ring 4 from the cap 3. As such, if the cap 3 is removed, it is clearly evidenced by the severing of the cap 3 and the tamper-evidence ring 4. Further, the severing of the cap 3 and tamper-evidence ring 4 may provide a tactile sensation for a user opening the housing 1 which may be generally beneficial, particularly for users with impaired vision.

The housing 1 may comprise at least one anti-rotation mechanism 15 to prevent rotation of the tamper-evidence ring 4 upon rotation of the cap 3. Additionally, or alternatively, the housing 1 may comprise at least one axial retention mechanism 16 configured to axially retain the tamper-evidence ring 4 upon removal of the cap 3. Thus, once attached, the tamper-evidence ring 4 may not be significantly movable in relation to the body 2 without severing the cap 3 and tamper-evidence ring 4.

Providing both an anti-rotation mechanism 15 and an axial retention mechanism 16 in combination may restrict the movement of the tamper-evidence ring 4 such that the severing of the tamper-evidence ring 4 and the cap 3 is more abrupt. Hence, for example, where frangible connectors 17 are used to connect between the tamper-evidence ring 4 and cap 3, they may be more readily broken simultaneously to provide more distinct haptic feedback to a user. For example, the rotational resistance may suddenly give and a click may be heard or felt by a user due to the simultaneous release of the connectors. In contrast, where the tamper-evidence ring 4 is allowed to move either axially or rotationally, it may allow the connectors 17 to break at different times or positions thereby diluting the haptic feedback and providing a less satisfactory response for a user.

Further, providing axial retention and anti-rotation may prevent movement of the tamper-evidence ring 4 following removal of the cap 3, thereby providing the housing 1 with a more solid feeling construction when the cap 3 is removed. This may improve the perceived quality of the housing and the product more generally.

Further still, the anti-rotation of the tamper-evidence ring 4 may allow the external profile of the housing to be maintained once the cap 3 has been removed. This may be particularly advantageous when the tamper-evidence ring 4 and body 2 have corresponding external shapes which require some rotational or axial alignment.

As noted above, the cap assembly 5 may comprise the cap 3 and the tamper-evidence ring 4. The tamper-evidence ring 4 may comprise a full annular band which is concentrically arranged around the central axis 5 and configured to engage with the body 2, for example, via the axial retention mechanism 16 and the anti-rotation mechanism 15. The direct engagement of the axial retention mechanism 16 and the anti-rotation mechanism 15 may occur only as the cap 3 is removed and the corresponding features of the body 2 and tamper-evidence ring 4 are urged into contact with one another, or may be present following the attachment of the cap assembly 5 to the body 2.

The tamper-evidence ring 4 may be joined to the cap 3 by one or more frangible portions which are configured to break when a sufficient mechanical force is applied between the cap 3 and ring 4. The tamper-evidence ring 4 and cap 3 may form a unitary body such that they are fabricated from a continuous, optionally homogenous, structure. In some embodiments, the tamper-evidence ring 4 and cap 3 may be co-formed as a single object, for example, by injection moulding.

The tamper-evidence ring 4 and cap 3 may be adjoined or attached to one another via a plurality of severable connectors 17 which extend therebetween and provide the frangible portion. The severable connectors 17 may be configured to break upon rotation and/or axial separation of the cap 3 from the body 2.

Figure 5:
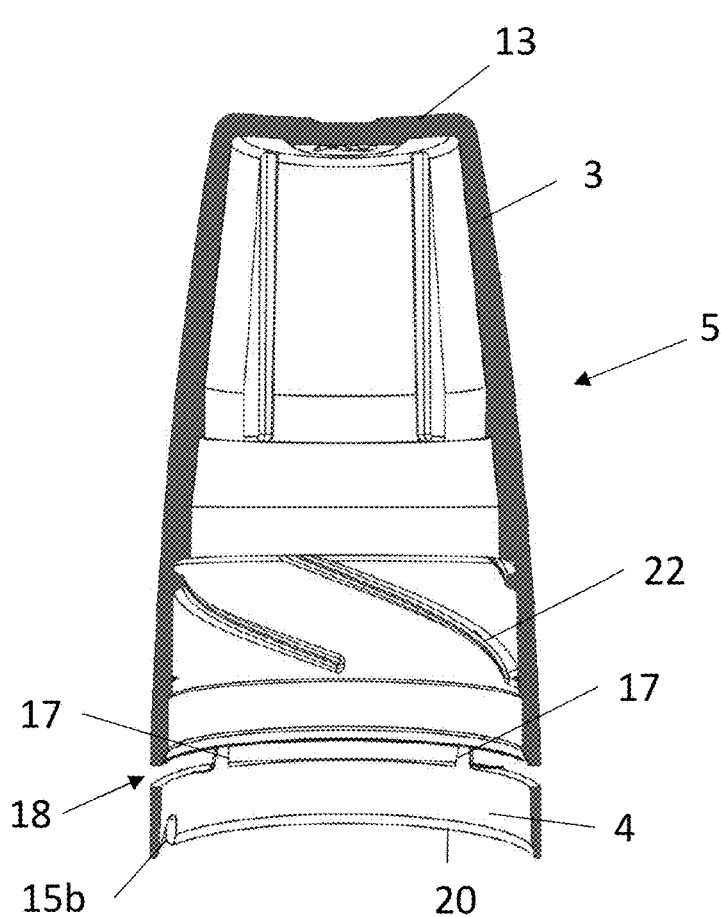
FIG. 5 shows a longitudinal section of the cap assembly prior to attachment to the body.

As best seen in FIG. 5, the tamper-evidence ring 4 may be separated from the cap 3 by an annular gap 18. The annular gap may be bridged by the plurality of connectors 17 which extend between the tamper-evidence ring 4 and the cap 3. It will be appreciated that the size, shape and number of connectors 17 will be predetermined and application specific and will, in combination, determine the force required to the sever the ring 4 and the cap 3. In the embodiment shown there are four connectors 17, but this may vary and, in some embodiments, there may be between two and eight connectors, or 3 and 5 connectors, for example. The connectors 17 may be circumferentially distributed around the tamper-evidence ring 4 and located at a corner region thereof, which is described in further detail below in connection with FIG. 6.

As shown, the connectors 17 may be elongate members which extend generally parallel to the central axis 6. In some embodiments, the connectors 17 may taper along the length to provide a preferential breaking point which, in the embodiment shown in FIG. 5, is provided proximate the cap 3.

The connectors 17 may extend from an axial end face of the tamper-evidence ring 4 which is located opposite and facing the corresponding axial end face of the rim of the cap 3. The connectors 17 have a first end attached to the tamper-evidence ring 4 and a second end which attaches to the cap 3. The taper is continuous between the first and second ends. The taper may be provided on an outer surface of the connectors 17 so as to taper radially inwards and/or on a side surface so as to taper circumferentially. The connectors 17 are shown as being generally rectangular in cross-section but this is not a limitation and other cross-sectional shapes may be possible.

Due to the taper, the cross-section area of the connector 17 where it joins the rim of the cap 3 is reduced compared to the connection provided at the first end so that the connector 17 breaks at the junction between the rim of the cap 3 and connector 17. In doing so, the cap 3 is provided with a substantially flat axial end surface once removed allowing it to be handled more readily and without interference from any stubs of the connector 17 which might otherwise be present if the connector 17 broke at a mid-point. The absence of the connector stubs may, for example, allow the cap 3 to be more readily placed into a pocket without snagging or be put on a surface face down once removed. It will be appreciated that a preferential weakening may be provided by means other than a taper, such as a narrowing of the connector 17 or the provision of a score line, for example.

Referring to FIGS. 1, 2, 5 and 6, the tamper-evidence ring 4 is shown as comprising a full annular band of material, e.g. a plastics material, having an axial length and radial thickness in relation to the principal axis 6 of the housing 1. As noted, the ring 4 may be axially spaced from the cap 3 by a generally annular gap which is bridged by a plurality of severable connectors 17. The free end of the ring 4 may be separated from the body 2 by a further annular gap 19 such that the ring 4 is generally only supported by the connectors 17 and the attachment of the cap 3 to the body 2, which is described further below. In some embodiments, the cap assembly 5 may not comprise an annular gap and the ring 4 may be a continuation of the cap 3 separated only by an annular recess in the wall of the cap assembly, or a plurality of perforations, for example.

Referring to FIG. 5, it can be seen that the radial thickness of the tamper-evidence ring 4 tapers towards the lower edge thereof, i.e. the free end 9. As such, the terminal peripheral edge rim of the tamper-evidence ring 4 is narrower than the main sectional thickness. The taper 20 is provided on the inner surface of the ring 4 such that the outer surface maintains a constant profile in longitudinal section to help maintain the flush outer profile of the housing 1. The taper 20 may be provided to allow the ring to receive the body more readily when the cap assembly 5 is mounted to the body 2.

A similar taper to that of taper 20 may be provided on the rim of the cap 3, thereby reducing the thickness of the cap 3 at the rim. It will be noted that the tamper-evidence ring 4 is radially thinner than the cap 3 as the mechanical strength required of the tamper-evidence ring 4 is reduced, and the thinner construction allows the tamper-evidence ring to deform more readily when being fitted over the axial retention projection 16a.

The attachment between the cap 3 to the body 2 may be achieved directly and/or using the tamper-evidence ring 4. The direct attachment may be achieved by any suitable means such as a threaded engagement, bayonet fitting, friction or interference fit, for example. The attachment may be rotational or linear or a combination thereof.

Figure 3:
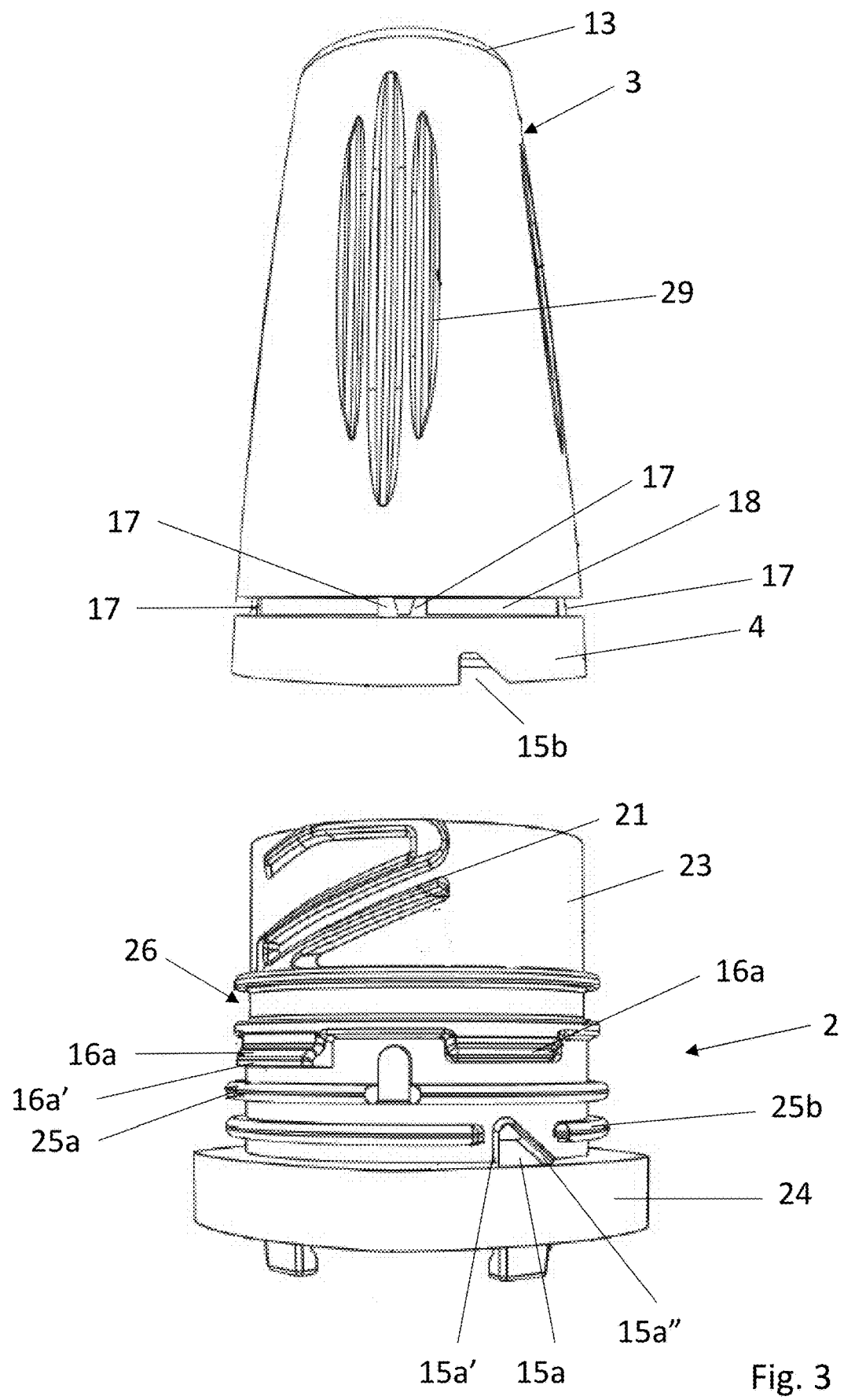
FIG. 3 shows an exploded view of the cap assembly and body of the housing of FIG. 1.

An example of a threaded engagement is shown in FIG. 3 which shows a thread 21 on the body 2, and FIG. 5 which shows the corresponding thread 22 on an internal surface of the cap 3. Hence, in the embodiment shown, the removal of the cap 3 requires rotation about the principal axis 6 by a user (typically by hand), which results in the axial and circumferential displacement of the cap 3 relative to the body 2 and the severing of the connectors 17.

With reference to FIGS. 3 and 4, the body 2 may comprise an inner body portion 23 and an outer body portion 24. The inner body portion 23 may be configured to be received within the cap 3 when the cap assembly 5 is mounted to the body 2 and comprise an elongate cylindrical hollow member. The inner body portion 23 may be concentrically aligned with (or define) the principal axis 6 of the housing 1 and comprise an outer surface which is provided in opposing relation to a corresponding internal surface of the cap 3 and tamper-evidence ring 4 when assembled.

The outer surface of the inner body portion 23 may comprise one or more of the thread 21, the axial retention projection 16a, the anti-rotation projection 15a, and one or more spacers 25a, 25b for maintaining the shape and radial spacing of the tamper-evidence ring 4 in relation to the body 2. The outer surface may also provide one or more sealing features for providing the hermetic seal, such as channel 26 in which the O-ring 14 is located, as described above.

The axial retention mechanism 16 may comprise one or more projections 16a which extend radially from the outer surface of the inner body portion body 23 towards the internal surface of the tamper-evidence ring 4. The projections 16a may be configured to engage with a corresponding feature or surface of the tamper-evidence ring 4 such that axial movement of the tamper-evidence ring 4 is prevented in normal use. As such, the projections 16a may prevent the tamper-evidence ring 4 from being removed from the body 2 when the cap 3 is removed.

In the embodiment shown in FIG. 3, the projections 16a are provided as a plurality of circumferentially extending teeth which are distributed around the circumference at a common axial location so as to be provided in a common plane. The projections extend radially into the annular gap 18 that separates the tamper-evidence ring 4 and cap 3.

The longitudinal section of the projections 16a (in relation to the principal axis 6) can be seen in FIG. 4 which shows the underside of the projection 16a that bears against the upper surface of the tamper-evidence ring 4 to provide a restraining surface 16a' which extends in the normal plane of the longitudinal axis 6.

The upper surface of the projection 16a which faces the rim of the cap 3 may comprise a sloped surface 16a". The sloped surface 16a" may be configured to receive the free end 9 of the tamper-evidence ring 4 as the cap assembly 5 is attached to the body 2, thereby allowing it to deform and/or expand and slide over the projections 16a during assembly. In other words, the combined sloped surfaces 16a" of the axial retention projections 16a may provide a divergent landing platform for receiving and expanding the tamper-evidence ring 4 during assembly.

The embodiment shown in the Figures includes four axial-retention projections 16a. However, it will be appreciated that more or fewer projections may be used in other embodiments. The axial-retention projections 16a may be uniformly or non-uniformly circumferentially distributed about the inner body portion 23.

The radial extent of the projections 16a may be less than the radial position of the outer surface of the cap 3 and/or tamper-evidence ring 4 such that they do not project outwardly and beyond the outer surface of the housing 1. However, in some embodiments, the projections 16a may be viewed through the annular gap 18 from an exterior of the housing 1 to determine whether they are engaged.

The anti-rotation mechanism 15 is configured to prevent the rotation of the tamper-evidence ring 4 once located on the body 2. In particular, the anti-rotation mechanism 15 is provided to prevent the rotation of the tamper-evidence ring 4 as the cap 3 is being rotated for removal from the body 2 and severance of the tamper-evidence ring 4. The anti-rotation mechanism 15 may comprise one or more projections 15a which extend axially and engage with corresponding features 15b of the tamper-evidence ring 4 so as to prevent relative rotation between the body 2 and tamper-evidence ring 4 following removal of the cap 3.

In the embodiment shown, the anti-rotation mechanism comprises a stud 15a which extends radially out of the inner body portion 23 and includes axial length to provide at least one circumferentially facing surface 15a' for engaging with a corresponding opposing circumferential surface 15b' of the tamper-evidence ring 4. The stud 15a is attached to the radially outwardly facing surface of the inner body portion 23 and an axially facing surface of a flange portion which defines a shoulder between the outer most external surface 24 of the body 2 and the outer surface of the inner body portion 23.

As can be seen, the stud 15a may be ramp-shaped such that a first surface of the stud which faces in a first direction, e.g. clockwise when viewed end-on from the cap end, is parallel with the longitudinal axis 6 and so prevents an anti-clockwise rotation of the cap 3 when being removed, and a ramped surface 15a" on the circumferentially opposing side of the stud 15a to provide a surface which faces axially and circumferentially towards the cap 3. The ramped surface 15a" is configured to receive the free-end edge of the tamper-evidence ring 4 when the cap assembly 5 is being mounted to the inner body portion 23 thereby forcing the tamper-evidence ring 4 to deform and locally expand such that it can pass over the stud 15a until the notch 15b and stud 15a are rotationally aligned. Once aligned, the tamper-evidence ring 4 returns to its original non-deformed state so as to receive and enclose the stud 15a. At this point the tamper-evidence ring 4 is prevented from being rotated.

In the embodiment shown in FIG. 3, the part of the anti-rotation mechanism 15 provided by the tamper-evidence ring 4 is a notch 15b located in the free-end edge thereof. As shown, the notch 15b may extend through the full radial thickness of the tamper-evidence ring 4 so as to be exposed on the exterior of the housing 1 to allow a user or person assembling the housing 1 to determine whether the anti-rotation mechanism 15 is properly engaged.

The radial projection of the stud 15*a* may be equal to or less than the radial extent of the tamper-evidence ring 4 such that the stud 15*a* is either flush or radially inwards of the outer surface of the tamper-evidence ring 4 when attached.

The anti-rotation projection 15*a* may be located anywhere around the circumference of the tamper-evidence ring 4 and there may be a plurality of similar circumferentially distributed projections.

The body 2 may be provided with one or more spacers 25*a,b* to maintain the radial separation between the tamper-evidence ring 4 and body 2, and to help maintain the shape and position of the tamper-evidence ring 4. As shown in FIG. 3, the one or more spacers 25*a,b* may comprise an annular projection in the form of a lip or flange which extends radially from the outer surface of the inner body portion 23 towards the inner surface of the tamper-evidence ring 4. Where there is a plurality of the spacers 25*a,b*, as per FIG. 3, they may be axially separated such that a first spacer 25*a* is provided towards the cap end of the tamper-evidence ring 4, and the second spacer 25*b* is provided towards the free end. The spacer members 25*a,b* are broadly similar to one another having corresponding radial and axial dimensions but this is not a limitation and the sizes and shapes may differ. The free end spacer 25*b* may be provided with a suitably shaped and sized arcuate notch to receive the anti-rotation stud 15*a*. Hence, the stud 15*a* may be located between terminal ends of adjacent portions of the spacer projection 25*b*.

It will be appreciated that in some embodiments the spacer members 25*a,b* may be partially or broken annuluses and may be provided by a castellated annulus or a circular array of pedestals, for example.

Figure 6:
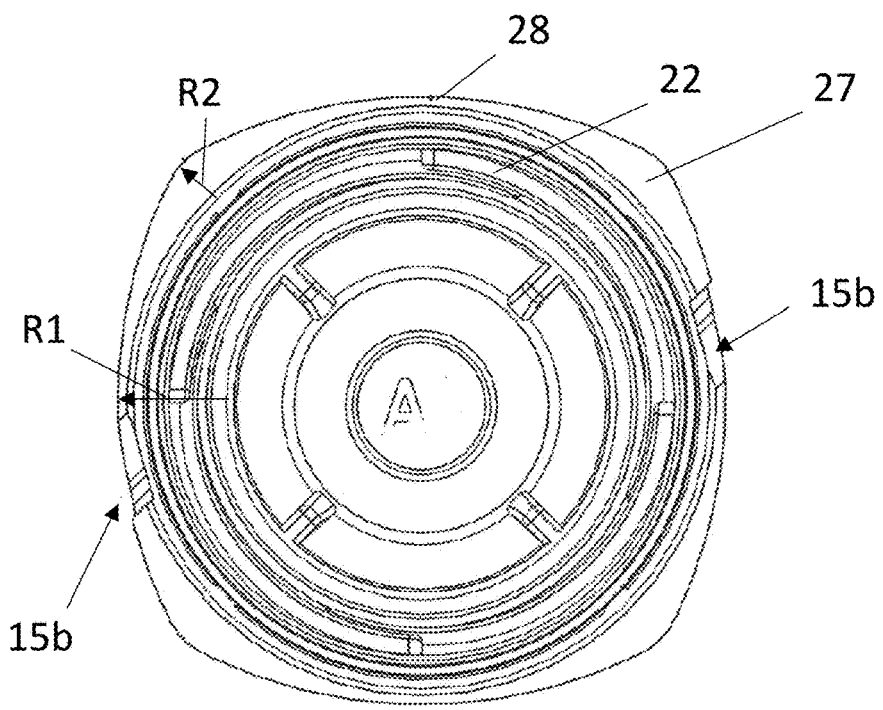
FIG. 6 shows an end-on internal view of the cap assembly.

With reference to FIGS. 1, 4 and 6, the tamper evidence ring 4 may be coaxial with the principal axis 6 of the housing 1 and the housing 1 may comprise a radially outer surface 24 and an inner body portion 23 which faces an opposing surface of the cap 3 and tamper-evidence ring 4. As can be seen, the inner body portion 23 may be generally cylindrical such that the radial separation between the inner surface of the cap 3 and tamper-evidence ring 4 and the body 2 is generally circumferentially uniform (with the exception of local protrusions, for example).

The outer surface 24 of the body 2, cap 3 and tamper-evidence ring 4 may take any shape as desired for aesthetic or handling purposes. In the embodiment shown in FIG. 6, the outer surfaces comprise a lobed profile in the form of a rounded square when viewed end on, i.e. transverse to the principal axis, and includes a plurality of circumferentially distributed lobes 27 provided by the corner regions. The lobes 27 may provide additional purchase for a user to grasp and rotate the cap 3 relative to the body 2 by hand. It will be appreciated that the external surfaces of the cap 3, main body 2 and tamper-evidence ring 4 may comprise corresponding cross-sectional profiles so as to maintain the flush outer contour of the housing 1.

To provide the rounded square profile, the radial distance between the outermost external surface of the cap assembly 5 and the central axis 6 of the housing 1 at each axial location may vary circumferentially. The rounded square shown in FIG. 6 comprises a plurality of corner regions 27 which are connected by curved edges 28. In the embodiment shown, the edges 28 which extend between the corner regions 27 are continuously curved and may include a constant radius of curvature R1 which is greater than the radius of the inner surface of the cap assembly which may be generally circular. The corner regions 27 may be defined by a second, smaller radius of curvature R2.

It will be appreciated that there may be a greater or fewer number of corner regions 27 than the four which are depicted in FIG. 6, and the cap 3 may comprise other gripping features to aid the engagement with a user's hand, such as the elongate grooves 29 shown in FIG. 3.

In order to provide the non-round profile of the cap assembly, it may be advantageous to vary the radial thickness of the tamper-evidence ring 4 circumferentially. As such, the tamper-evidence ring 4 may be thicker in some circumferential locations, e.g. the corner regions 27, than others, e.g. the edges 28. In contrast, the inner surface of the cap 3 and tamper-evidence ring 4 may be circular and allow a threaded engagement between the cap 3 and the body 2, as described above.

Although not evident in FIG. 6, the connectors 17 may be provided at the corner regions 27 of the tamper-evidence ring 4. Providing the connectors 17 at the corner regions 27 provides increased rigidity at the point of connection between the cap 3 and tamper-evidence ring 4, thereby providing an increased stability to the tamper-evidence ring 4 during removal of the cap 3 and breaking of the connectors 17. In some embodiments, the connectors 17 may be provided at a circumferential apex of the corner regions 27.

Figure 8:
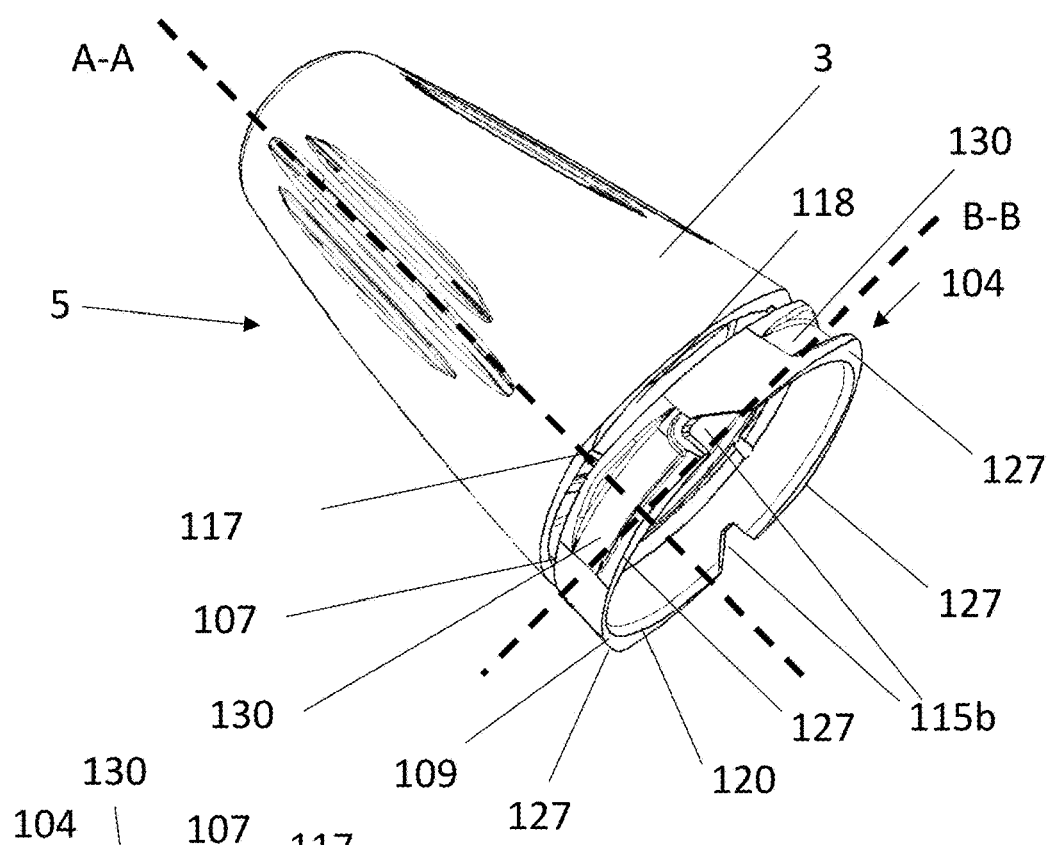
FIG. 8 shows a perspective view of an alternative cap assembly according to the present invention.
Figure 9:
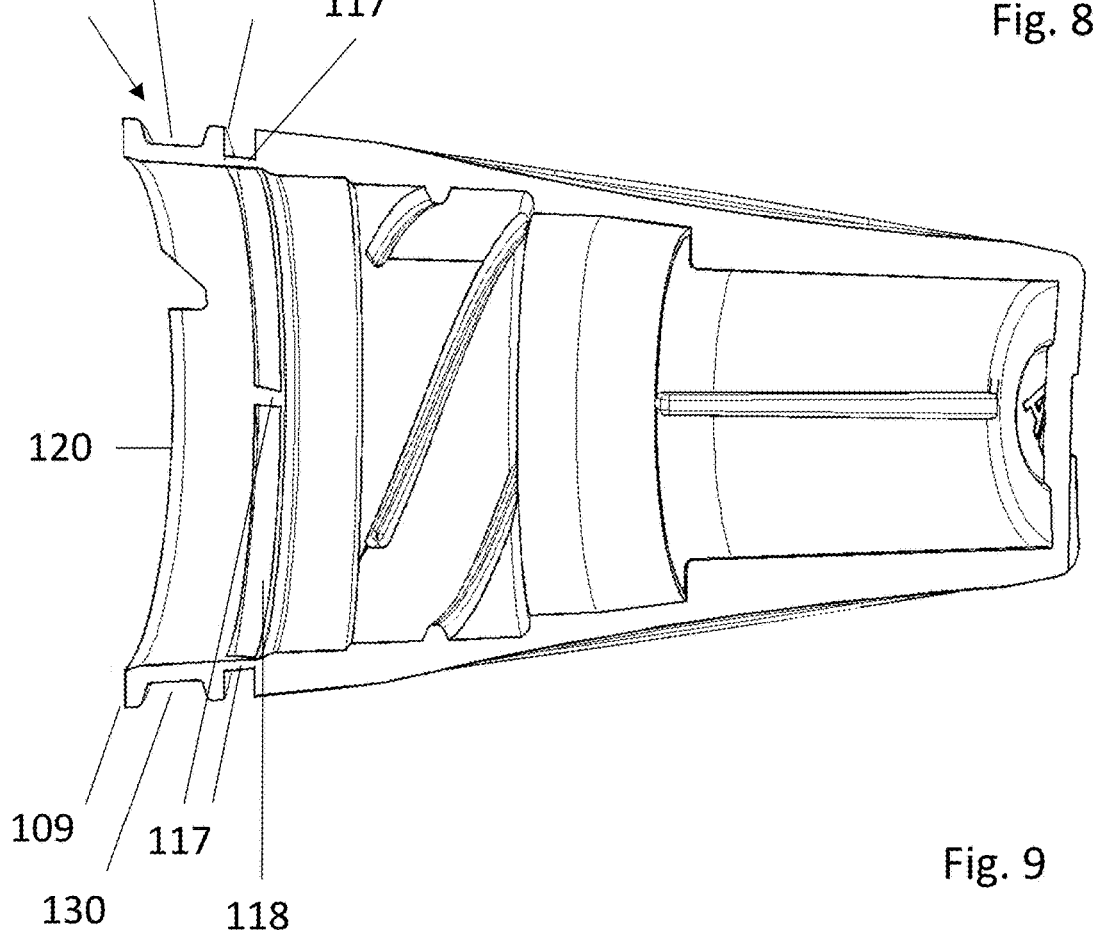
FIG. 9 shows a longitudinal cross-sectional view of the cap assembly of FIG. 8.
Figure 10:
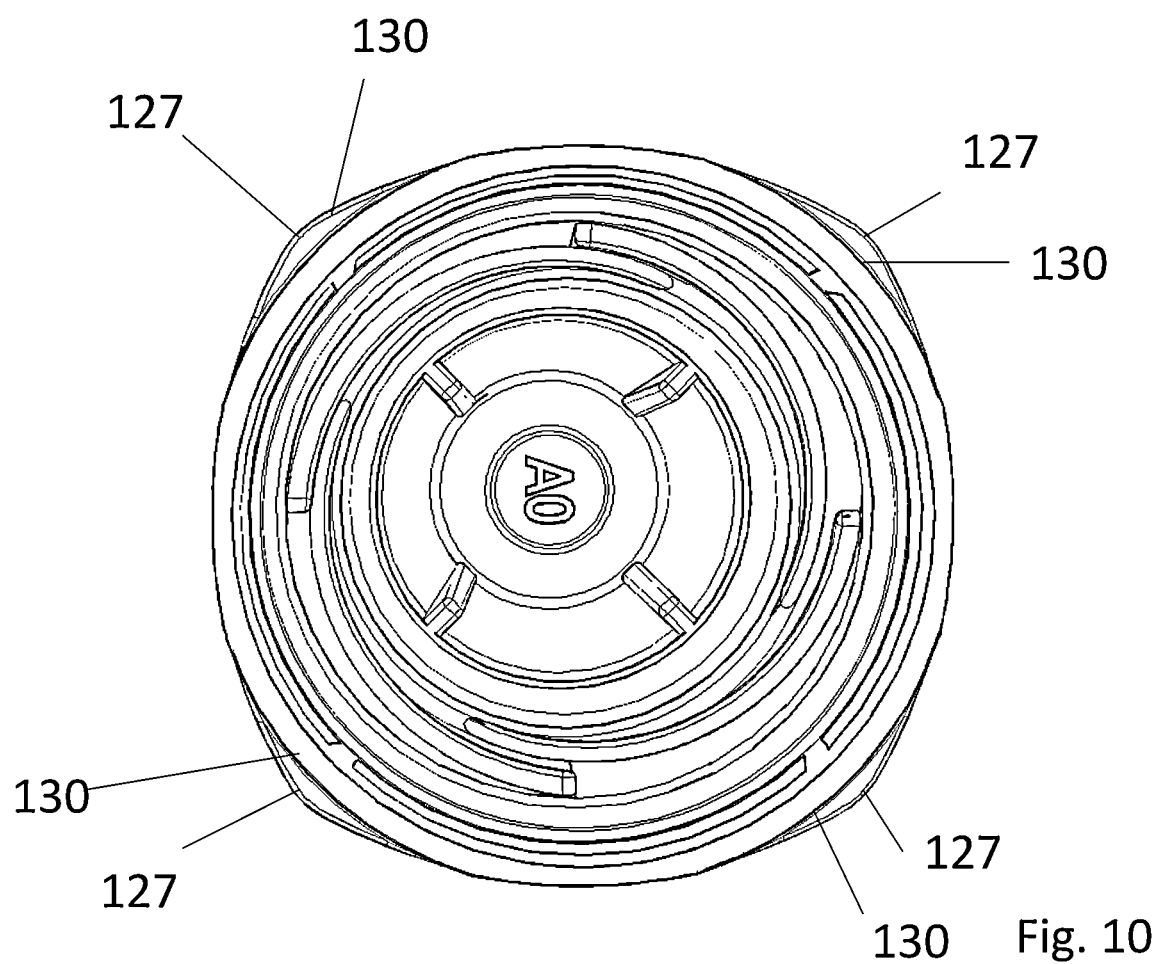
FIG. 10 shows a transverse cross-sectional view of the tamper-evidence ring of FIG. 8.

FIGS. 8, 9 and 10 show an alternative embodiment of the tamper-evidence ring 104, FIG. 9 is a cross section along line A-A and FIG. 10 a cross section along line B-B. As will be described in detail below, the tamper-evidence ring 104 of this embodiment differs from the previous tamper-evidence ring 4 in that the corner regions 127 are provided with recesses, other features are common between the two tamper-evidence rings 4,104 and as such will be similarly numbered, advances by 100, below.

With reference to FIGS. 8 and 9, the tamper-evidence ring 104 may comprise a cap-end 107 which is proximate and/or adjacent to the open end 8 of the cap 3, and a free-end 109 (which may be referred to as a body-end) which may receive and be proximate and/or adjacent to the body 2.

The tamper-evidence ring 104 may be joined to the cap 3 by one or more frangible portions which are configured to break when a sufficient mechanical force is applied between the cap 3 and ring 104. The tamper-evidence ring 104 and cap 3 may form a unitary body such that they are fabricated from a continuous, optionally homogenous, structure. In some embodiments, the tamper-evidence ring 104 and cap 3 may be co-formed as a single object, for example, by injection moulding.

The tamper-evidence ring 104 and cap 3 may be adjoined or attached to one another via a plurality of severable connectors 117 which extend therebetween and provide the frangible portion. The severable connectors 117 may be configured to break upon rotation and/or axial separation of the cap 3 from the body 2.

As best seen in FIG. 9, the tamper-evidence ring 104 may be separated from the cap 3 by an annular gap 118. The annular gap may be bridged by the plurality of connectors 117 which extend between the tamper-evidence ring 104 and the cap 3. It will be appreciated that the size, shape and number of connectors 117 will be predetermined and application specific and will, in combination, determine the force required to the sever the ring 104 and the cap 3. In the embodiment shown there are four connectors 117, but this may vary and, in some embodiments, there may be between two and eight connectors, or three and five connectors, for example. The connectors 117 may be circumferentially distributed around the tamper-evidence ring 104 and located at a corner region thereof, which is described in further detail below.

As shown, the connectors 117 may be elongate members which extend generally parallel to the central axis. In some embodiments, the connectors 117 may taper along the length to provide a preferential breaking point which, in the embodiment is provided proximate the cap 3.

The connectors 117 may extend from an axial end face of the tamper-evidence ring 104 which is located opposite and facing the corresponding axial end face of the rim of the cap 3. The connectors 117 have a first end attached to the tamper-evidence ring 104 and a second end which attaches to the cap 3. The taper is continuous between the first and second ends. The taper may be provided on an outer surface of the connectors 117 so as to taper radially inwards and/or on a side surface so as to taper circumferentially. The connectors 117 are shown as being generally rectangular in cross-section but this is not a limitation and other cross-sectional shapes may be possible.

Due to the taper, the cross-section area of the connector 117 where it joins the rim of the cap 3 is reduced compared to the connection provided at the first end so that the connector 117 breaks at the junction between the rim of the cap 3 and connector 117. In doing so, the cap 3 is provided with a substantially flat axial end surface once removed allowing it to be handled more readily and without interference from any stubs of the connector 117 which might otherwise be present if the connector 117 broke at a midpoint. The absence of the connector stubs may, for example, allow the cap 3 to be more readily placed into a pocket without snagging or be put on a surface face down once removed. It will be appreciated that a preferential weakening may be provided by means other than a taper, such as a narrowing of the connector 117 or the provision of a score line, for example.

Referring to FIGS. 8, 9 and 10, the tamper-evidence ring 104 is shown as comprising a full annular band of material, e.g. a plastics material, having an axial length and radial thickness in relation to the principal axis 6 of the housing 1. As noted, the ring 104 may be axially spaced from the cap 3 by a generally annular gap 118 which is bridged by a plurality of severable connectors 117. The free end of the ring 104 may be separated from the body 2 by a further annular gap such that the ring 104 is generally only supported by the connectors 117 and the attachment of the cap 3 to the body 2, which is described further below. In some embodiments, the cap assembly 5 may not comprise an annular gap and the ring 104 may be a continuation of the cap 3 separated only by an annular recess in the wall of the cap assembly, or a plurality of perforations, for example.

Referring to FIG. 9, it can be seen that the radial thickness of the tamper-evidence ring 104 tapers towards the lower edge thereof, i.e. the free end 109. As such, the terminal peripheral edge rim of the tamper-evidence ring 104 is narrower than the main sectional thickness. The taper 120 is provided on the inner surface of the ring 104 such that the outer surface maintains a constant profile in longitudinal section to help maintain the flush outer profile of the housing 1. The taper 120 may be provided to allow the 104 ring to receive the body more readily when the cap assembly 5 is mounted to the body 2.

In the embodiment shown in FIG. 8, the part of the anti-rotation mechanism provided by the tamper-evidence ring 104 is a notch 115b located in the free-end edge thereof. As shown, the notch 115b may extend through the full radial thickness of the tamper-evidence ring 104 so as to be exposed on the exterior of the housing 1 to allow a user or person assembling the housing 1 to determine whether the anti-rotation mechanism 15 is properly engaged.

It will be appreciated that the part of the anti-rotation mechanism 15 provided on the body 2 are the same for both embodiments of the tamper-evidence ring.

The outer surface 124 of the tamper-evidence ring 104 may take any shape as desired for aesthetic or handling purposes. In the embodiment shown in FIG. 8, the outer surfaces comprise a lobed profile in the form of a rounded square when viewed end on, i.e. transverse to the principal axis, and includes a plurality of circumferentially distributed lobes 127 provided by the corner regions. The lobes 127 may provide additional purchase for a user to grasp and rotate the cap 3 relative to the body 2 by hand. It will be appreciated that the external surfaces of the cap 3, main body 2 and tamper-evidence ring 104 may comprise corresponding cross-sectional profiles so as to maintain the flush outer contour of the housing 1.

In order to provide the non-round profile of the cap assembly, it may be advantageous to vary the radial thickness of the tamper-evidence ring 104 circumferentially. As such, the tamper-evidence ring 104 may be thicker in some circumferential locations, e.g. corner regions 127, than others, e.g. edges 128. In contrast, the inner surface of the cap 3 and tamper-evidence ring 104 may be circular and allow a threaded engagement between the cap 3 and the body 2, as described above.

In this embodiment the corner regions 127 each comprise a recess 130 that extends circumferentially through the lobe 127. Each of the recesses 130 are axially aligned and the depth of each recess 130 varies circumferentially such that for the axial extent of the recesses 130, the external surface of the tamper-evidence ring has a round profile.

As shown in FIG. 8, the connectors 117 may be provided at the corner regions 127 of the tamper-evidence ring 104. Providing the connectors 117 at the corner regions 127 provides increased rigidity at the point of connection between the cap 3 and tamper-evidence ring 104, thereby providing an increased stability to the tamper-evidence ring 104 during removal of the cap 3 and breaking of the connectors 117. In some embodiments, the connectors 117 may be provided at a circumferential apex of the corner regions 127.

FIG. 7 shows a longitudinal cross-section of the housing 1 in which there is located a catheter 71, in particular, an intermittent female urinary catheter as known in the art. The details of the catheter are not important for the present invention and will not be described further here.

The main body and cap assembly may be made from a plastics material and may be formed using an injection moulding process. However, other methods of manufacture may be possible.

To assemble the housing, the catheter 71 may first be loaded into the body 2 such that only a portion of the catheter 71 is exposed for aiding removal. The cap assembly 5 is located over the inner body portion 23 and lowered until the corresponding threads 21, 22 of the body 2 and cap 3 can engage. Rotating the cap 3 further results in the cap assembly 5 and tapered rim of the free-end of the tamper-evidence ring 4,104 contacting the upper ramp formations of the axial retention projection 16a causing the tamper-evidence ring 4,104 to deform and expand over the projections 16a. Continued rotation of the cap assembly 5 lowers the tamper-evidence ring 4,104 further until the free end 9,109 contacts the anti-rotation projection 15a and deflects the corner region of the tamper-evidence ring 104 adjacent to the notch 15b,115b. The deflection of the corner region allows the tamper-evidence ring 4,104 to pass over the projection 15a until the anti-rotation projection 15a aligns with the notch 15b,115b allowing the corner region to spring back into place and latch around the anti-rotation projection 15a to prevent rotation. At the anti-rotation mechanism latches, the axial retention projections 16a enter the annular gap 18,118 and latch the tamper-evident ring 4 to prevent axial separation.

To remove the cap 3, a user simply grasps the body 2 and cap 3 and counter-rotates the two components to cause the cap 3 to axially separate from the body 2 by virtue of the thread engagement. In an initial phase, the rotation of the cap 3 is inhibited by the anti-rotation mechanism 15 and axial retention mechanism 16 which act against the axial and rotational movement exerted on the cap 3. Once a predetermined amount of torque is applied by the user, the connectors 17,117 break, and the cap 3 is free to rotate and be removed, thereby breaking the seal 14 and exposing the catheter 71, for use.

The one or more embodiments are described above by way of example only. Many variations are possible without departing from the scope of protection afforded by the appended claims.

The invention claimed is:

1. A catheter assembly comprising a urinary catheter and a housing for the catheter, the housing comprising:
   a body;
   a cap assembly comprising a cap and a tamper-evidence ring,
   wherein the cap is attached to the body and the tamper-evidence ring in an unopened configuration and is configured to be irreversibly detached from the tamper-evidence ring when the cap is removed from the body,
   the housing further comprising at least one anti-rotation mechanism to prevent rotation of the tamper-evidence ring upon rotation of the cap, and at least one axial retention mechanism configured to axially retain the tamper-evidence ring when irreversibly detached from the cap;
   wherein the anti-rotation mechanism is configured to allow the tamper-evidence ring to rotate in a first rotational direction and obstruct rotation in a second rotational direction;
   wherein the anti-rotation mechanism further comprises a circumferentially facing ramp to allow rotation in the first direction.

2. The catheter assembly of claim 1, wherein the tamper-evidence ring is attached to the cap via a plurality of severable connectors which extend therebetween, wherein the severable connectors are configured to break upon rotation and/or axial separation of the cap from the body, wherein the tamper-evidence ring is separated from the cap via an annular gap which is bridged by the plurality of severable connectors.

3. The catheter assembly of claim 1, wherein the tamper-evidence ring forms a unitary body with the cap.

4. The catheter assembly of claim 1, wherein the axial retention mechanism comprises at least one radial projection which extends from the body to engage with the tamper-evidence ring, wherein the at least one axial retention projection is positioned between the tamper-evidence ring and cap.

5. The catheter assembly of claim 4, comprising a plurality of circumferentially distributed axial retention projections.

6. The catheter assembly of claim 1, wherein the anti-rotation mechanism comprises at least one radial projection which extends from the body and engages with the tamper-evidence ring.

7. The catheter assembly of claim 6, wherein the anti-rotation mechanism and the axial retention mechanism are axially separated from one another.

8. A catheter assembly comprising a urinary catheter and a housing for the catheter, the housing comprising:
   a body:
   a cap assembly comprising a cap and a tamper-evidence ring,
   wherein the cap is attached to the body and the tamper-evidence ring in an unopened configuration and is configured to be irreversibly detached from the tamper-evidence ring when the cap is removed from the body,
   the housing further comprising at least one anti-rotation mechanism to prevent rotation of the tamper-evidence ring upon rotation of the cap, and at least one axial retention mechanism configured to axially retain the tamper-evidence ring when irreversibly detached from the cap;
   wherein the anti-rotation mechanism is configured to allow the tamper-evidence ring to rotate in a first rotational direction and obstruct rotation in a second rotational direction;
   wherein at least one radial projection comprises circumferentially facing ramps on a first surface.

9. The catheter assembly of claim 8 wherein the at least one radial projection comprises a second surface on a circumferentially opposing side of the at least one radial projection to the first surface, wherein the second surface is perpendicular to the second rotational direction.

10. The catheter assembly claim 1, wherein either or both of the axial retention mechanism and the anti-rotational mechanism are viewable from the exterior of the housing when the cap is attached to the body.

11. A catheter assembly comprising a urinary catheter and a housing for the catheter, the housing comprising:
   a body:
   a cap assembly comprising a cap and a tamper-evidence ring,
   wherein the cap is attached to the body and the tamper-evidence ring in an unopened configuration and is configured to be irreversibly detached from the tamper-evidence ring when the cap is removed from the body,
   the housing further comprising at least one anti-rotation mechanism to prevent rotation of the tamper-evidence ring upon rotation of the cap, and at least one axial retention mechanism configured to axially retain the tamper-evidence ring when irreversibly detached from the cap;
   wherein the body comprises at least one spacer radially inwards of the tamper-evidence ring, the spacer being configured to limit the radial deflection of the tamper-evidence ring.

12. The catheter assembly of claim 11, wherein the spacer comprises an annular projection which extends radially from the body.

13. The catheter assembly of claim 12, wherein the annular projection is a partial annulus having opposing ends, wherein the at least one radial anti-rotation projection is provided between the opposing terminal ends.

14. A catheter assembly comprising a urinary catheter and a housing for the catheter, the housing comprising:
   a body:
   a cap assembly comprising a cap and a tamper-evidence ring, wherein the cap is attached to the body and the tamper-evidence ring in an unopened configuration and is configured to be irreversibly detached from the tamper-evidence ring when the cap is removed from the body, the housing further comprising at least one anti-rotation mechanism to prevent rotation of the tamper-evidence ring upon rotation of the cap, and at least one axial retention mechanism configured to axially retain the tamper-evidence ring when irreversibly detached from the cap wherein the body comprises an outermost external surface which is axially adjacent to the tamper-evidence ring and separated therefrom by an annular gap, wherein the outermost external surface of the body, the tamper-evidence ring and the cap are non-circular and have corresponding external surfaces.

15. The catheter assembly of claim 1 wherein the radial thickness of the tamper-evidence ring varies circumferentially.

16. A catheter assembly comprising a urinary catheter and a housing for the catheter, the housing comprising:
a body;
a cap assembly comprising a cap and a tamper-evidence ring,
wherein the cap is attached to the body and the tamper-evidence ring in an unopened configuration and is configured to be irreversibly detached from the tamper-evidence ring when the cap is removed from the body,
the housing further comprising at least one anti-rotation mechanism to prevent rotation of the tamper-evidence ring upon rotation of the cap, and at least one axial retention mechanism configured to axially retain the tamper-evidence ring when irreversibly detached from the cap wherein the radial thickness of the tamper-evidence ring varies circumferentially;

wherein the tamper-evidence ring comprises at least one corner region and a plurality of severable connectors are provided at the corner region.

17. The catheter assembly of claim 16 wherein the least one corner region comprises a recess, wherein the recess is on an external surface of the tamper-evidence ring and extends circumferentially.

18. The catheter assembly of claim 1, wherein the axial retention projection comprises a cap-facing surface which is axially sloped to as to provide a divergent surface for receiving the tamper-evidence ring during an assembly of the housing.

* * * * *